(12) United States Patent
Takekoshi et al.

(10) Patent No.: US 8,181,657 B2
(45) Date of Patent: May 22, 2012

(54) PLACEMENT METHOD AND PLACEMENT SYSTEM

(75) Inventors: Satoshi Takekoshi, Hachioji (JP); Naruto Shinkai, Kawasaki (JP); Takaaki Gono, Hachioji (JP); Yosuke Yoshimoto, Hachioji (JP)

(73) Assignee: Olympus Medical Systems Corp. (JP)

( * ) Notice: Subject to any disclaimer, the term of this patent is extended or adjusted under 35 U.S.C. 154(b) by 1273 days.

(21) Appl. No.: 11/861,767

(22) Filed: Sep. 26, 2007

(65) Prior Publication Data
US 2009/0082622 A1   Mar. 26, 2009

(51) Int. Cl.
 A61B 1/00    (2006.01)
 A61B 19/00   (2006.01)
 A61F 6/06    (2006.01)
(52) U.S. Cl. .................. 128/898; 128/831; 600/104
(58) Field of Classification Search .................. 128/898, 128/830–841; 606/191–198; 600/104–106, 600/114–118, 135, 156–159
See application file for complete search history.

(56) References Cited

U.S. PATENT DOCUMENTS

| | | | | |
|---|---|---|---|---|
| 4,611,602 A | * | 9/1986 | Bolduc | 600/560 |
| 5,303,719 A | * | 4/1994 | Wilk et al. | 128/898 |
| 2005/0240211 A1 | * | 10/2005 | Sporri et al. | 606/193 |
| 2008/0167664 A1 | * | 7/2008 | Payne et al. | 606/135 |
| 2008/0178889 A1 | * | 7/2008 | Tal | 128/831 |
| 2008/0178891 A1 | * | 7/2008 | McGuckin | 128/831 |
| 2009/0171268 A1 | * | 7/2009 | Williams et al. | 604/26 |

FOREIGN PATENT DOCUMENTS

| | | |
|---|---|---|
| WO | WO 96/39950 | 12/1996 |
| WO | WO 03/099149 | 12/2003 |

* cited by examiner

*Primary Examiner* — Matthew J Kasztejna
*Assistant Examiner* — Ryan Henderson
(74) *Attorney, Agent, or Firm* — Ostrolenk Faber LLP

(57) ABSTRACT

A placement method includes inserting an endoscope into a body, blocking a tubular tissue in the body with a distal end of the endoscope, pressurizing a detection target space between a placement member which is placed in the tubular tissue and blocks the tubular tissue and the distal end of the endoscope via a channel of the endoscope, and detecting a pressure state in the detection target space.

8 Claims, 10 Drawing Sheets

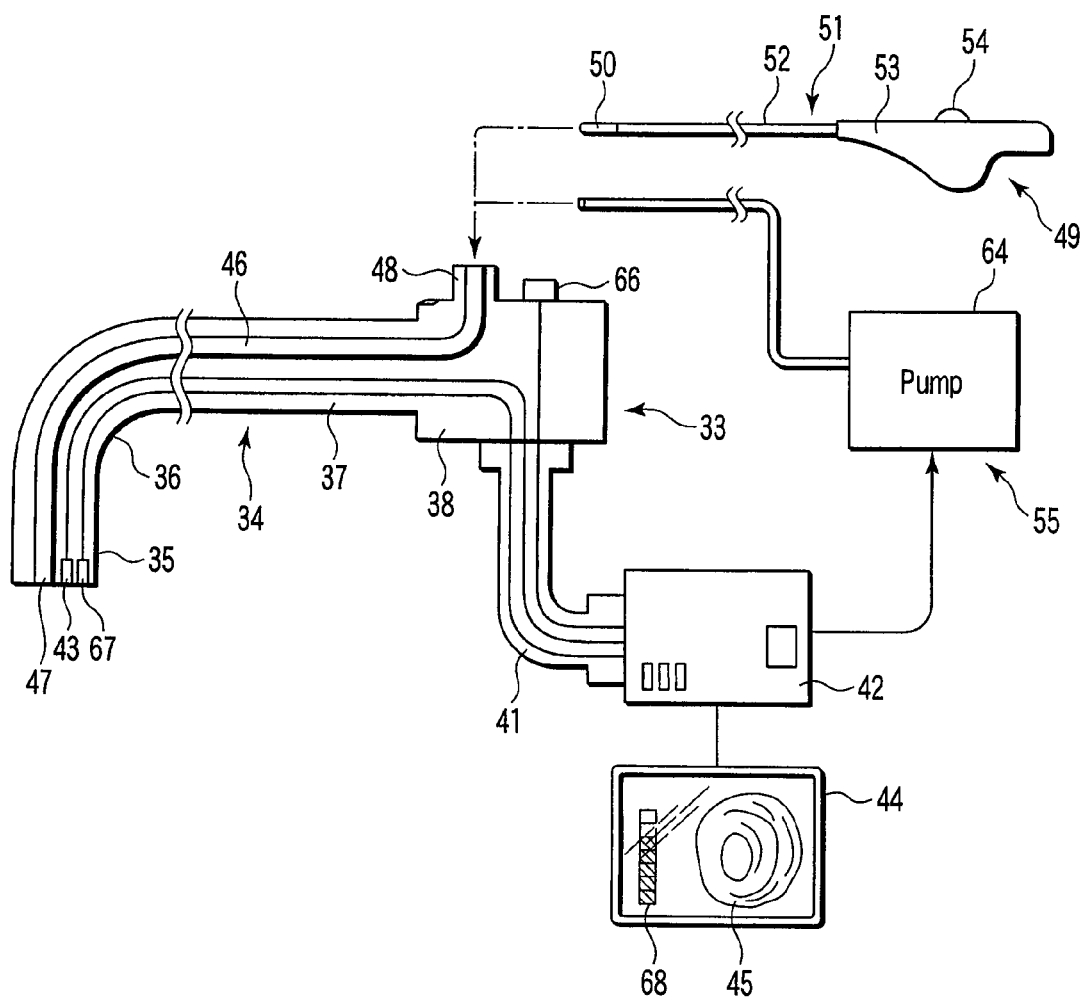
F I G. 11
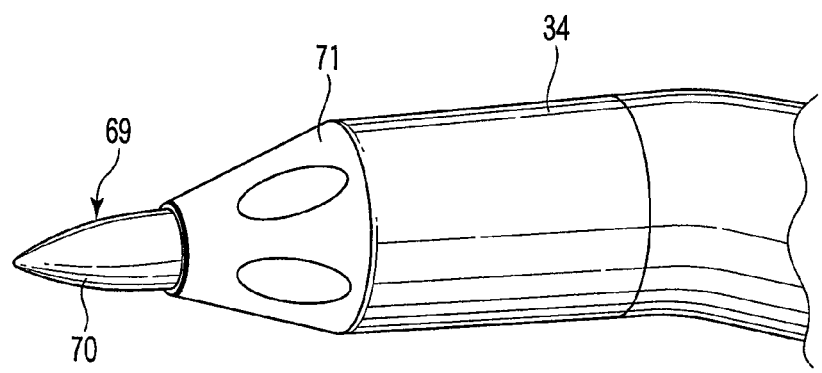
F I G. 12

PLACEMENT METHOD AND PLACEMENT SYSTEM

BACKGROUND OF THE INVENTION

1. Field of the Invention

The present invention relates to a placement method and a placement system for placing a placement member in a tubular tissue in a body to block a tubular tissue.

2. Description of the Related Art

Various procedures have been carried out to place a placement member in a tubular tissue in a body in to block the tubular tissue. Such procedures include, for example, a contraceptive operation wherein uterine tubes is blocked to obstruct the transportation of ova, a hepatic artery embolization wherein a hepatic artery is blocked to stop blood flow to cancer cells and destroy the cancer cells, and an emphysema treatment wherein a bronchial tube is blocked to cause the return of air. Moreover, a system for the contraceptive operation has been disclosed in the International Publication No. 2003/99149 pamphlet, and a system for blocking a vessel branch has been disclosed in the International Publication No. 96/39950 pamphlet.

BRIEF SUMMARY OF THE INVENTION

In an aspect of the present invention, a placement method includes: inserting an endoscope into a body; blocking a tubular tissue in the body with a distal end of the endoscope; pressurizing a detection target space between a placement member which is placed in the tubular tissue and blocks the tubular tissue and the distal end of the endoscope via a channel of the endoscope; and detecting a pressure state in the detection target space.

In another aspect of the present invention, a placement system includes: an endoscope configured to be inserted into a body and including a distal end configured to block a tubular tissue in the body; a placement device including a placement member configured to block the tubular tissue and a placement instrument configured to place the placement member in the tubular tissue; a pressurization device configured to pressurize a detection target space between the placement member which is placed in the tubular tissue and the distal end of the endoscope which blocks the tubular tissue via a channel of the endoscope; and a detection device configured to detects a pressure state in the detecting target space.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 11 is a schematic diagram showing a placement system in a fifth embodiment of the present invention;

FIG. 12 is a perspective view showing the distal ends of an endoscope and an insertion aid instrument in a first referential embodiment of the present invention;

DETAILED DESCRIPTION OF THE INVENTION

Hereinafter, embodiments of the present invention will be described with reference to the drawings.

FIGS. 1 to 8 show a first embodiment of the present invention.

A placement method of the present embodiment concerns a contraceptive operation wherein a placement member is placed in the uterine tube to block the uterine tube, and includes checking whether the placement member is properly placed in the uterine tube.

Figure 1:
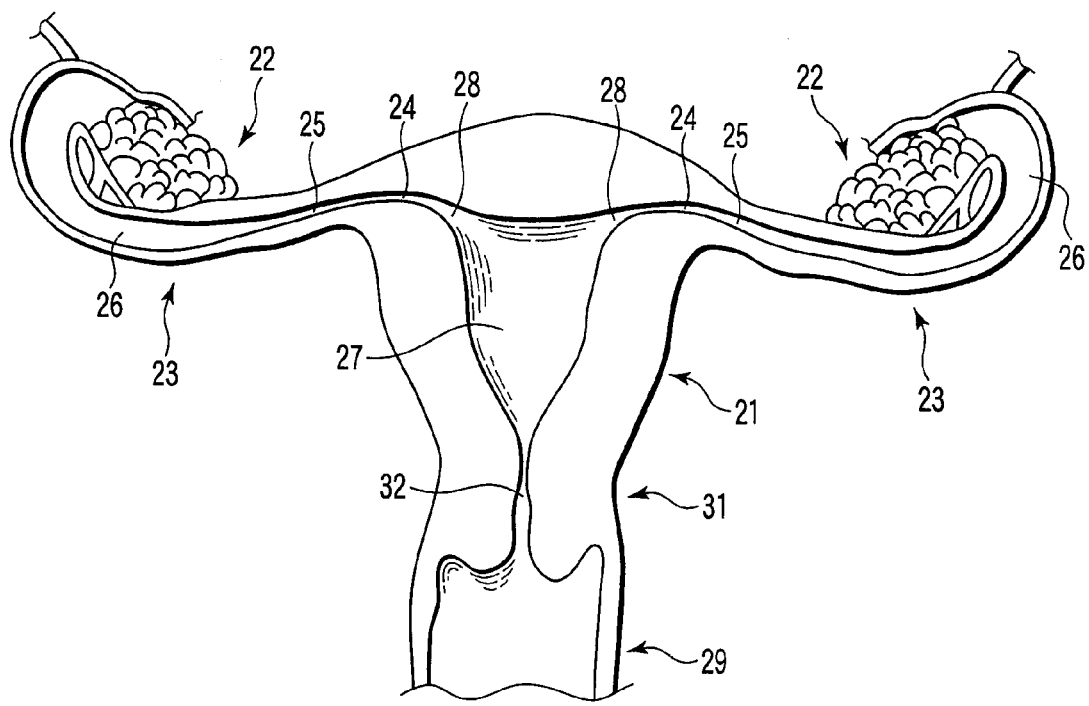
FIG. 1 is an anatomical diagram of the female genital organs.

Female genital organs targeted for the placement method will be explained referring to FIG. 1.

The Ovaries 22 are located on both lateral side of an upper part of the uterus 21, and both upper lateral parts of the uterus 21 are connected to both the ovaries 22 via the uterine tubes 23, respectively. The uterine tube 23 forms the interstitial portion 24, the isthmus 25 and the ampulla 26, from the uterus 21 toward the ovary 22. The uterine cavity 27 is formed by a lumen of the uterus 21, and the uterine tube ostia 28 forming entrances into the uterine tubes 23 are formed in both upper lateral parts of the uterine cavity 27. A lumen of the uterine tube 23 is narrower than the uterine cavity 27, and gradually becomes thinner in the interstitial portion 24, and then reaches a fixed thickness in the isthmus 25. On the other hand, a vagina 29 is located under the uterus 21, and a lower part of the uterus 21 is connected to the vagina 29 via a uterine cervix 31. A lumen of the uterine cavity 27 is connected to a lumen of the vagina 29 via a cervical canal 32 of the uterine cervix 31, which is narrow enough with respect to the inner cavities of the uterine cavity 27 and the vagina 29.

An ovum produced in the ovary 22 is moved to the uterine cavity 27 through the lumen of the uterine tube 23. A fertilized ovum is formed by the fertilization of the ovum with a sperm in the uterine cavity 27, and the fertilized ovum is implanted in the uterus 21, thereby causing pregnancy. Therefore, when the placement member is placed in the uterine tube 23 to block the uterine tubes 23 and obstruct the transportation of ova, pregnancy can be prevented. Here, when the blockage of the uterine tubes 23 by the placement member is insecure, ova might reach the uterine cavity 27, in which case secure contraception is difficult.

Figure 2:
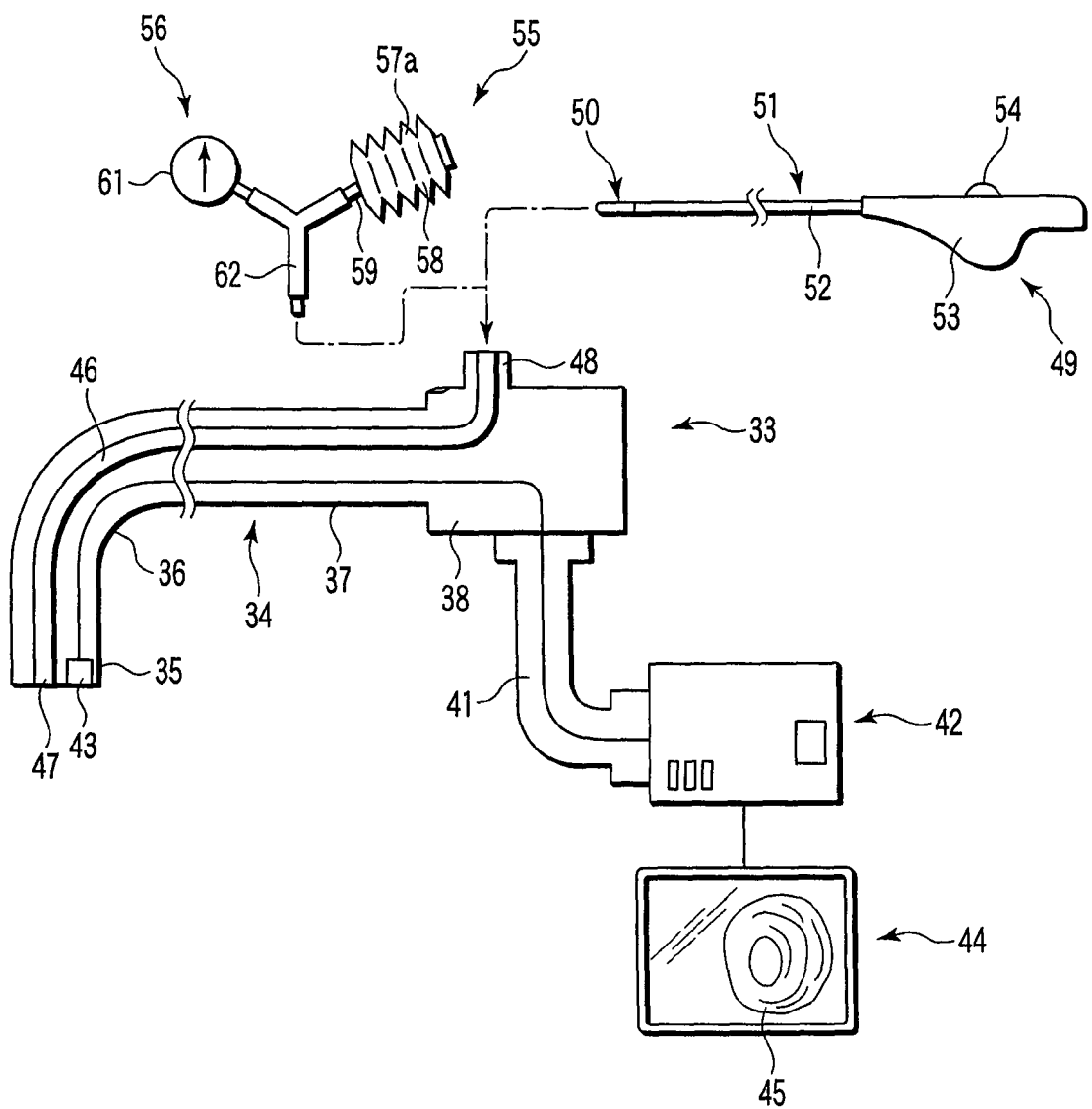
FIG. 2 is a schematic diagram showing a placement system in a first embodiment of the present invention.

A placement system for use in the placement method will be explained referring to FIG. 2.

Regarding an endoscope 33 of the placement system, the endoscope 33 is a flexible scope. That is, the endoscope 33 includes an elongated endoscope insertion portion 34 to be inserted into the body. In the endoscope insertion portion 34, a distal rigid portion 35, a bending portion 36 to be operated to bend and a long flexible insertion tube portion 37 is connected in order from its distal side. Here, the outside diameter of the endoscope insertion portion 34 is set so that the distal end of the endoscope insertion portion 34 is inserted into the uterine tube ostium 28 and fitted into the uterine tube 23 to block the uterine tube 23. An endoscope operation portion 38 gripped and operated by one hand of an operator is connected to the proximal end of the endoscope insertion portion 34. A bending operation knob is disposed in the endoscope operation portion 38 for the bending operation of the bending portion 36. A universal cord 41 extends from the endoscope operation portion 38 and is connected to a video processor 42. Here, an image pick up unit 43 for picking up an observation image is incorporated in the distal rigid portion 35 of the endoscope 33. An image signal obtained in the image pick up unit 43 is output to the video processor 42 via a signal line inserted through the endoscope 33, and the video processor 42 processes the image signal to display an observation image 45 on a monitor 44. Moreover, an accessory channel 46 extends from the distal end of the endoscope insertion portion 34 to the endoscope operation portion 38. The distal end of the accessory channel 46 is open and forms a channel opening 47 at the distal end of the endoscope insertion portion 34, and the proximal end of the accessory channel 46 is coupled to the inner end of a accessory insertion connecter 48 protruding in the endoscope operation portion 38.

Regarding a placement device 49 of the placement system, the placement device 49 is formed of the placement member and a placement instrument 51. The placement member is a circular blocking tube 50 whose one end is blocked, and is configured to be coaxially pushed into the uterine tube 23 to block the uterine tube 23. On the other hand, the placement instrument 51 includes an elongated insertion portion 52 to be inserted into the accessory channel 46 of the endoscope 33, and the blocking tube 50 is attached at the distal end of the insertion portion 52. An operation portion 53 is gripped and operated by one hand of the operator is connected to the proximal end of the insertion portion 52. The operation portion 53 is provided with a rotating dial 54, and the rotating dial 54 is configured to be rotationally operated to separate the blocking tube 50 from the distal end of the insertion portion 52.

The placement system is provided with a pressurization device 55 and a detection device 56, and the pressurization device 55 includes a non-return manual pump 57a. In the non-return manual pump 57a, a connection connecter 59 is connected to an elastic pleated bag member 58. The bag member 58 is provided with a non-return valve which only permits the passage of air from the outside to the inside, and the connection connecter 59 is provided with a non-return valve which only permits the passage of air from the inside to the outside. Moreover, the detection device 56 includes a pressure gauge 61. The non-return manual pump 57a and the pressure gauge 61 are connected to branch ends of a Y-shaped connecting tube 62. The proximal end of the connecting tube 62 is connectable to the accessory insertion connecter 48 of the endoscope 33. When the proximal end of the connecting tube 62 is connected to the accessory insertion connecter 48, the air can be emitted from the channel opening 47 via the connecting tube 62 and the accessory channel 46 through the compression of the non-return manual pump 57a. Further, the pressure value outside the channel opening 47 can be detected by the pressure gauge 61 via the connecting tube 62 and the accessory channel 46.

Figure 3:
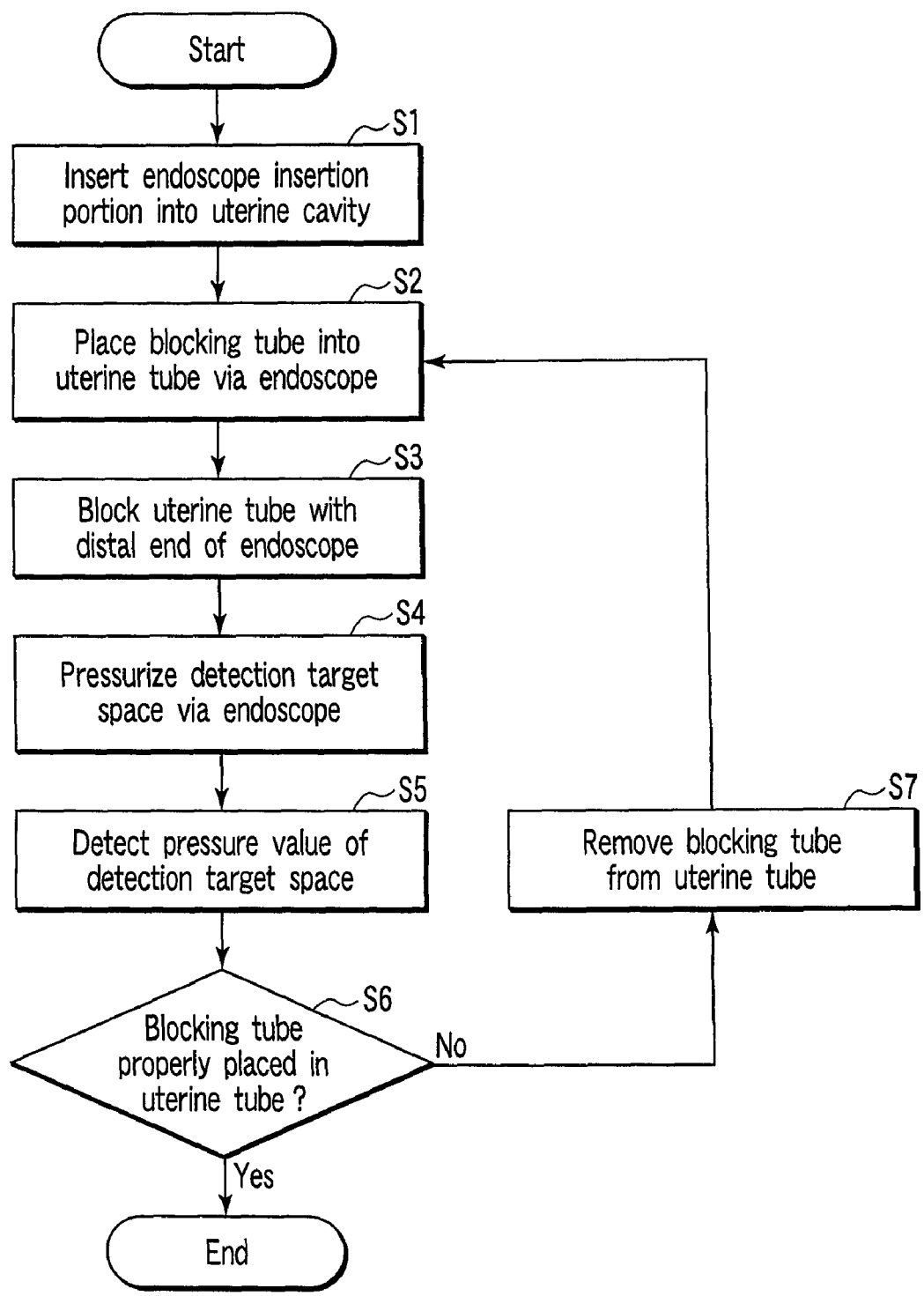
FIG. 3 is a flowchart showing a placement method in the first embodiment of the present invention.

The placement method of the present embodiment will be explained referring to FIG. 3.

Insertion Step (S1)

Figure 4:
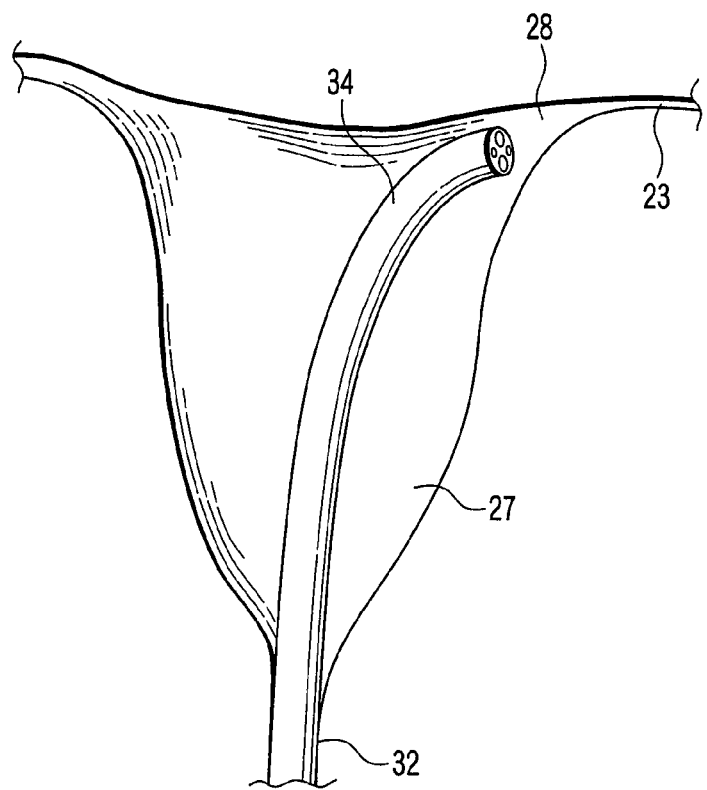
FIG. 4 is a schematic diagram showing an insertion step of the placement method in the first embodiment of the present invention.

As shown in FIG. 4, the endoscope insertion portion 34 is inserted into the uterine cavity 27 via the lumen of the vagina 29 and the cervical canal 32. Then, the distal end of the endoscope insertion portion 34 is placed face to the uterine tube ostium 28 while operating the bending portion 36 to bend.

Placement Step (S2)

Figure 5:
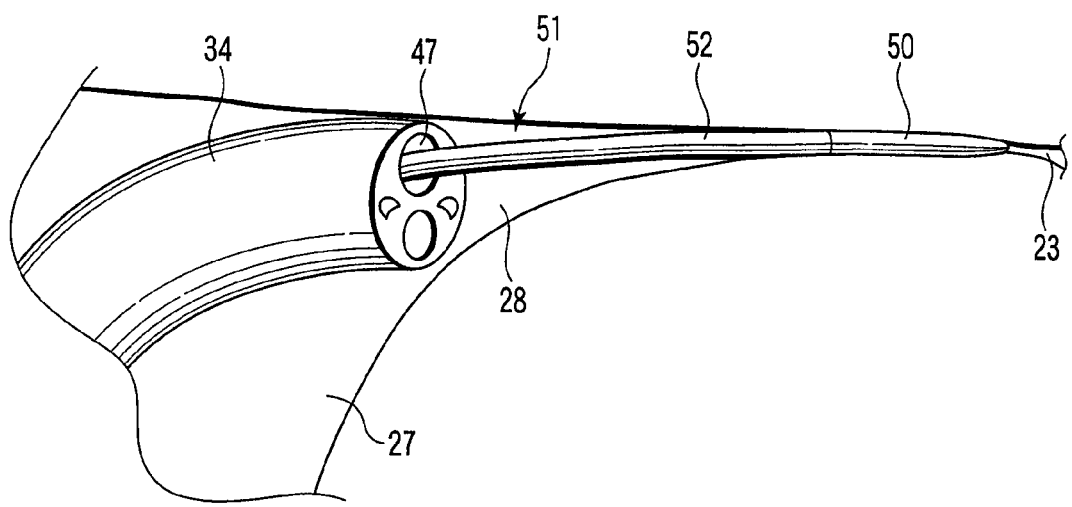
FIG. 5 is a schematic diagram showing a placement step of the placement method in the first embodiment of the present invention.

As shown in FIG. 5, the insertion portion 52 of the placement instrument 51 is inserted from the accessory insertion connecter 48 of the endoscope 33, and inserted through the accessory channel 46, and then projected from the channel opening 47. Further, the insertion portion 52 is moved forward under endoscopic observation, so that the blocking tube 50 at the distal end of the insertion portion 52 is inserted from the uterine tube ostium 28 into the uterine tube 23 and pushed into the tapering uterine tube 23. The forward movement of the insertion portion 52 is stopped when it is judged that the blocking tube 50 has reached an appropriate placement position, and the blocking tube 50 is separated from the placement instrument 51 and placed in the uterine tube 23. Then, the insertion portion 52 is moved back and removed from the accessory channel 46.

Blocking Step (S3)

Figure 6:
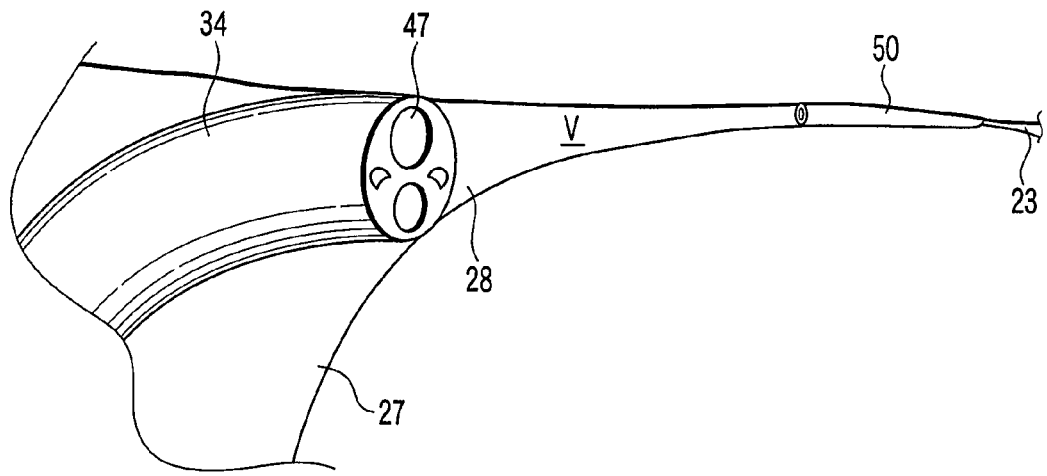
FIG. 6 is a schematic diagram showing a blocking step of the placement method in the first embodiment of the present invention.

As shown in FIG. 6, the distal end of the endoscope insertion portion 34 is inserted into the uterine tube ostium 28 and fitted into the uterine tube 23, and the uterine tube 23 is blocked with the distal end of the endoscope insertion portion 34. A space between the blocking tube 50 and the distal end of the endoscope insertion portion 34 in the uterine tube 23 is a detection target space V.

Pressurization Step (S4)

Figure 7:
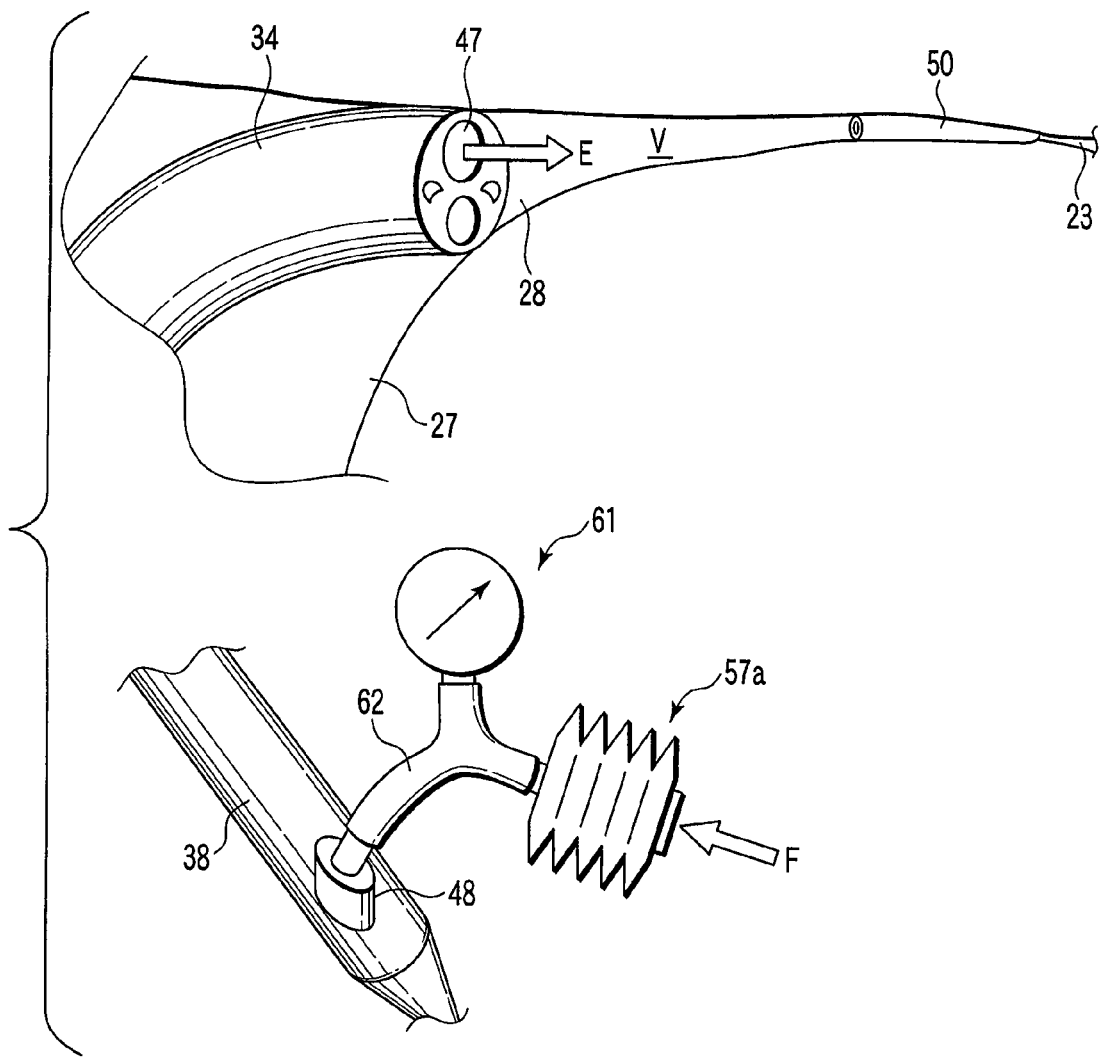
FIG. 7 is a schematic diagram showing a pressurization step and a detection step of the placement method in the first embodiment of the present invention.

As shown in FIG. 7, the proximal end of the connecting tube 62 is connected to the accessory insertion connecter 48 of the endoscope 33. Then, the non-return manual pump 57a is compressed as indicated by an arrow F in the drawing, and the air is supplied from the channel opening 47 into the detection target space V via the connecting tube 62 and the accessory channel 46 as indicated by an arrow E in the drawing, thereby pressurizing the detection target space V.

Then, the compressing operation of the non-return manual pump 57a is released.

Detection Step (S5)

As shown in FIG. 7, the pressure value in the detection target space V is detected by the pressure gauge 61 via the accessory channel 46 and the connecting tube 62.

Judgment Step (S6)

It is judged whether the blocking tube 50 is properly placed in the uterine tube 23.

Figure 8:
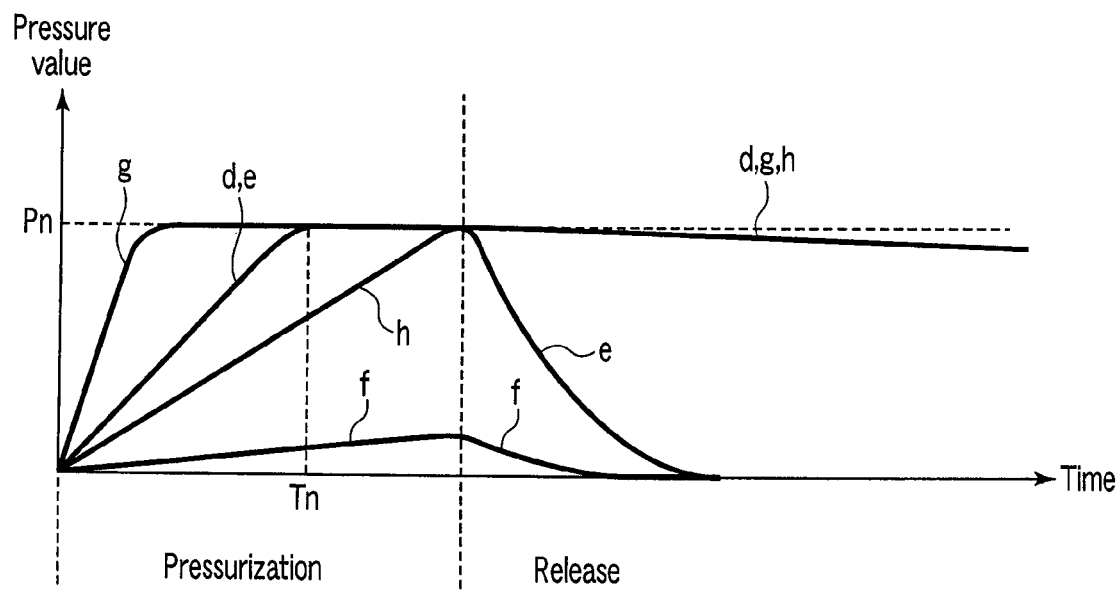
FIG. 8 is a graph for explaining a judgment step of the placement method in the first embodiment of the present invention.

That is, when the uterine tube 23 is securely blocked by the blocking tube 50, the pressure value increases to a criterion pressure value Pn by the pressurization of the detection target space V, and gently decreases from the criterion pressure value Pn after the release of the pressurization of the detection target space V, as indicated by d in the graph of FIG. 8. Conversely, when the uterine tube 23 is imperfectly blocked by the blocking tube 50, the air leaks from the detection target space V into the inner part of the uterine tube 23 beyond the blocking tube 50, and the pressure value sharply decreases from the criterion pressure value Pn after the release of the pressurization of the detection target space V, as indicated by e in the graph. Moreover, when the uterine tube 23 is hardly blocked by the blocking tube 50, the pressure value is hardly increased even by the pressurization of the detection target space V and does not reach the criterion pressure value Pn, as indicated by f in the graph. Thus, it is possible to judge whether the uterine tube 23 is securely blocked by the blocking tube 50 in accordance with the change of the pressure value of the detection target space V.

Furthermore, when the uterine tube 23 is securely blocked by the blocking tube 50, the volume of the detection target space V takes a certain criterion volume value when the blocking tube 50 is disposed at the appropriate placement position, and a certain criterion compressing operation amount, that is, a certain criterion time Tn is required to reach the criterion pressure value Pn. Conversely, when the blocking tube 50 is shifted toward the uterine tube ostium 28 side from the appropriate placement position, the volume of the detection target space V is smaller than the criterion volume, so that the time required to reach the criterion pressure value Pn is shorter than the criterion time Tn, as indicated by g in the graph. On the other hand, when the blocking tube 50 is shifted toward the inner side of the uterine tube 23 from the appropriate placement position, the volume of the detection target space V is greater than the criterion volume, so that the time required to reach the criterion pressure value Pn is longer than the criterion time Tn, as indicated by h in the graph. Thus, it is possible to judge whether the blocking tube 50 is disposed at the appropriate position in accordance with the change of the pressure value of the detection target space V.

Removal Step (S7)

When the blocking tube 50 is not properly placed, the blocking tube 50 is removed by the use of forceps via the accessory channel 46 of the endoscope 33. Subsequently, the steps since the placement step are repeated to properly place the blocking tube 50.

Figure 9:
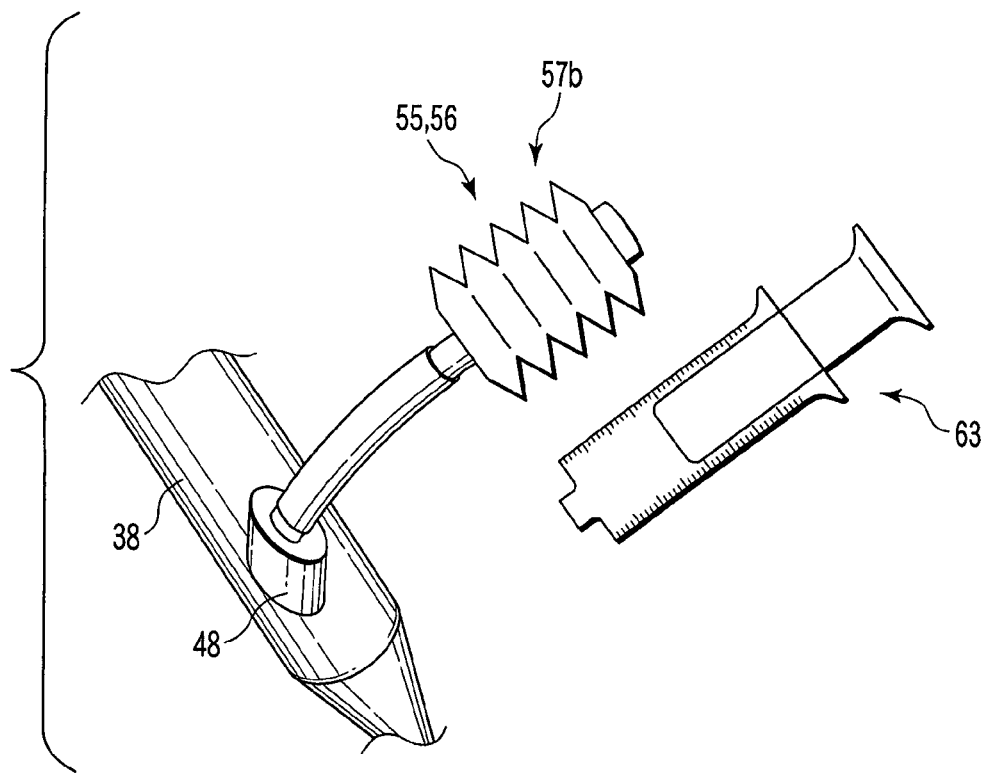
FIG. 9 is a schematic diagram showing a pressurization device and a detection device of a placement system in a second embodiment of the present invention.

FIG. 9 shows a second embodiment of the present invention.

In the pressurization device 55 and the detection device 56 of the placement system in the present embodiment, the connecting tube 62 includes no branching tube, and a connecting manual pump 57b is only connected to the connecting tube 62. No non-return valve is provided in the connecting manual pump 57b. That is, when the proximal end of the connecting tube 62 is connected to the accessory insertion connecter 48 of the endoscope 33, the internal space of the connecting manual pump 57b is connected to the detection target space V via the accessory channel 46 of the endoscope 33, and the pressure in the internal space of the connecting manual pump 57b is equal to the pressure in the detection target space V.

In a placement method of the present embodiment, the connecting manual pump 57b is compressed to pressurize the detection target space V in the pressurization step, and the pressure state of the detection target space V is detected in the detection step on the basis of reaction force against the compressing operation of the connecting manual pump 57b.

That is, when the uterine tube 23 is securely blocked by a blocking tube 50, the reaction force increases to a certain criterion reaction force in response to the compressing operation of the connecting manual pump 57b, and after the compressing operation is stopped, the reaction force gently decreases from the certain criterion reaction force. Conversely, when the uterine tube 23 is imperfectly blocked by the blocking tube 50, the reaction force sharply decreases from the certain criterion reaction force after the compressing operation is stopped. Moreover, when the uterine tube 23 is hardly blocked by the blocking tube 50, the reaction force is hardly increased even by the compressing operation of the connecting manual pump 57b and does not reach the criterion pressure value.

Furthermore, when the uterine tube 23 is securely blocked by the blocking tube 50, a certain criterion compressing operation amount is required to reach the criterion reaction force when the blocking tube 50 is disposed at the appropriate placement position. Conversely, when the blocking tube 50 is shifted toward the uterine tube ostium 28 side from the appropriate placement position, the compressing operation amount required to reach the criterion reaction force is smaller than the criterion compressing operation amount. On the other hand, when the blocking tube 50 is shifted toward the inner side of the uterine tube 23 from the appropriate placement position, the compressing operation amount required to reach the criterion reaction force is greater than the criterion compressing operation amount.

In addition, a manual piston-cylinder 63 may be used instead of the connecting manual pump 57b. When the piston-cylinder 63 is used, the compressing operation amount can be easily and accurately known.

A third embodiment of the present invention will be explained below.

In a placement method of the present embodiment, after an insertion step, a placement step is carried out after a blocking step is carried out, in contrast with the placement method of the first embodiment. That is, the endoscope insertion portion 34 is inserted into the uterine cavity 27, and the uterine tube 23 is blocked with the distal end of the endoscope insertion portion 34. Then, while the uterine tube 23 is being blocked with the distal end of the endoscope insertion portion 34, the blocking tube 50 is placed in the uterine tube 23 by the placement instrument 51 via the accessory channel 46 of the endoscope 33. Subsequently, the detection target space V is pressurized, and the pressure value in the detection target space V is detected, thereby whether the blocking tube 50 is placed at the appropriate placement position is judged. When the blocking tube 50 is not properly placed, the blocking tube 50 is removed, and the steps since the placement step are repeated to properly place the blocking tube 50.

Figure 10:
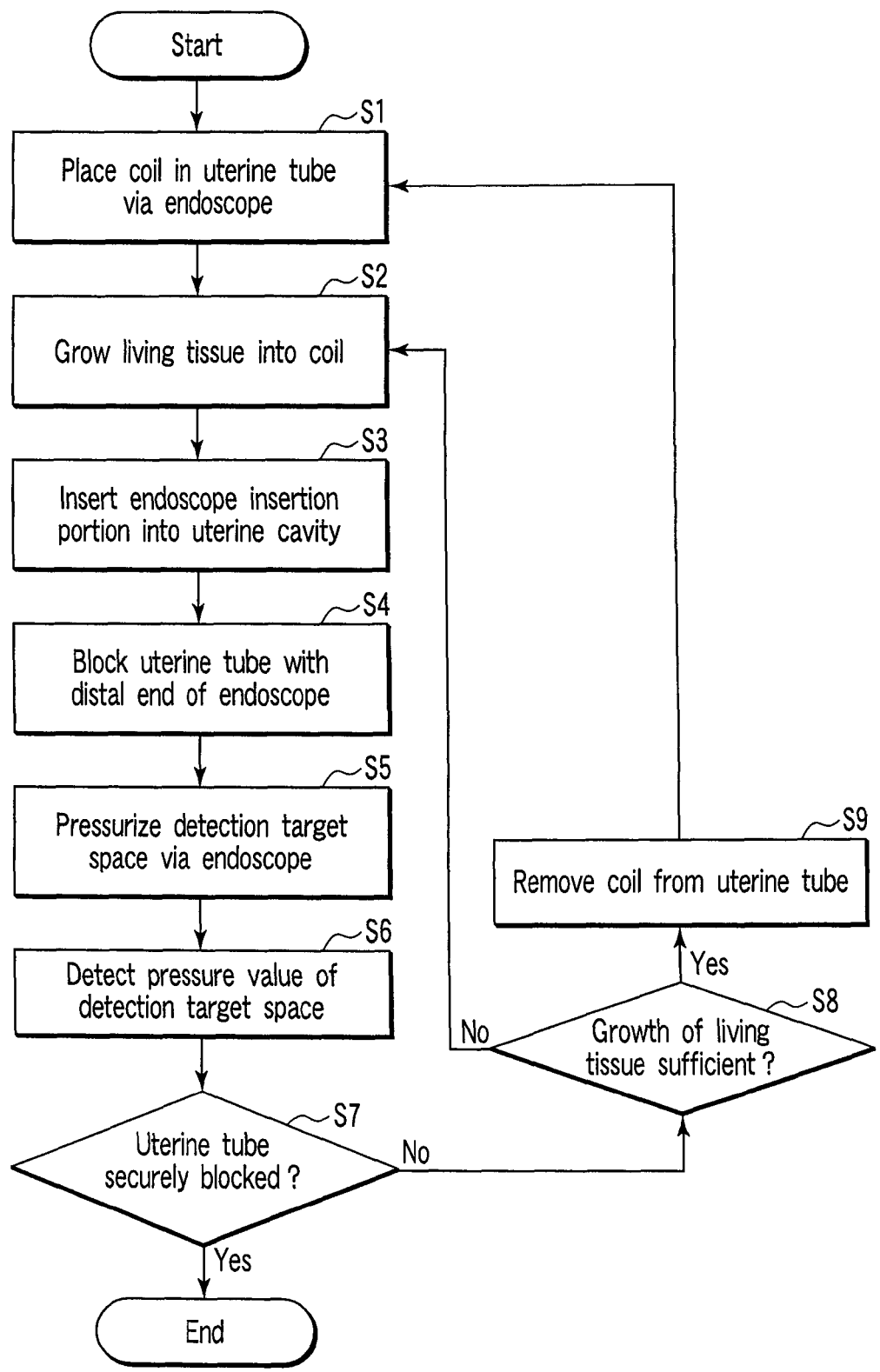
FIG. 10 is a flowchart showing a placement method in a fourth embodiment of the present invention.

FIG. 10 shows a fourth embodiment of the present invention.

In the placement device of the present embodiment, a circular tubular coil is used as the placement member. When the coil is pushed into and placed in the uterine tube 23, living tissue gradually grows into the coil, and the uterine tube 23 is blocked by the coil and the living tissue two or three months later.

A placement method of the present embodiment will be explained below.

Placement Step (S1)

The coil is previously placed in the uterine tube 23 via the accessory channel 46 of the endoscope 33 by a placement step similar to those in the first to third embodiments.

Growth Step (S2)

A living tissue grows into the coil.

Insertion step, blocking step, pressurization step, detection step, blockage judging step (S5 to S7)

At a time when the uterine tube 23 is considered to have been blocked by the growth of the living tissue, whether the uterine tube 23 is securely blocked is checked. That is, the endoscope insertion portion 34 is inserted into the uterine cavity 27, and the uterine tube 23 is blocked with the distal end of the endoscope insertion portion 34. Then, the detection target space V is pressurized, and the pressure value in the detection target space V is detected, thereby whether the uterine tube 23 is securely blocked is judged.

Growth Judging Step (S8)

When the uterine tube 23 is not securely blocked, the growth period of the living tissue is secured when the growth of the living tissue is considered to be still insufficient. In this case, whether the uterine tube 23 is securely blocked is again checked later.

Removal Step (S9)

When the growth of the living tissue is sufficient and the improper placement of the coil is considered to cause the insecure blockage of the uterine tube 23, the coil is removed from the uterine tube 23, and the coil is placed again.

FIG. 11 shows a fifth embodiment of the present invention.

In the pressurization device 55 of the present embodiment, an electrically driven pump 64 for supplying air is used. The electrically driven pump 64 is connected to the accessory insertion connecter 48 of the endoscope 33 via an air supply tube 65. An endoscope operation portion 38 is provided with a pressurization button 66. When the pressurization button 66 is depressed, a pressurization signal is output from the endoscope 33 to the video processor 42, and the electrically driven pump 64 is operated by the video processor 42. Air is supplied from the electrically driven pump 64 into the detection target space V via the air supply tube 65 and the accessory channel 46 of the endoscope 33 by the operation of the electrically driven pump 64, such that the detection target space V can be pressurized.

In the detection device 56, a pressure sensor 67 for detecting the pressure value in the detection target space V is provided at the distal end of the endoscope insertion portion 34. A detection signal is output from the pressure sensor 67 to the video processor 42 via the endoscope 33. The video processor 42 displays a pressure indication image 68 indicating the pressure value on the monitor 44 together with the observation image 45 on the basis of the detection signal. In the present embodiment, a bar graph is employed as the pressure indication image 68, but the pressure indication image 68 may be in any form.

A placement method of the present embodiment is substantially similar to that in the first embodiment. However, in the pressurization step, the pressurization button 66 of the endoscope operation portion 38 is depressed to operate the electrically driven pump 64, and air is supplied to the detection target space V to pressurize the detection target space V. Further, in the detection step, a pressure value is measured by the pressure sensor 67 at the distal end of the endoscope insertion portion 34, and the pressure value is displayed on the monitor 44. In the judgment step, whether the blocking tube 50 is properly placed in the uterine tube is judged on the basis of the pressure value displayed on the monitor 44.

In addition, while the pressure sensor 67 is provided at the distal end of the endoscope insertion portion 34 to directly detect the pressure value in the detection target space V in the present embodiment, the pressure sensor 67 may be disposed in the endoscope operation portion 38 to measure the pressure value in the accessory channel 46 such that the pressure of the detection target space V is indirectly measured.

Furthermore, an arithmetic unit may be connected to the video processor 42, store a criterion curve as indicated by d in the graph of FIG. 8 showing changes of the pressure value when the blocking tube 50 is properly placed in the uterine tube 23, compare a measured pressure value with the criterion curve, and judge whether the blocking tube 50 is properly placed in the uterine tube 23. In this case, the result of the judgment may be directly displayed on the monitor 44.

Figure 13:
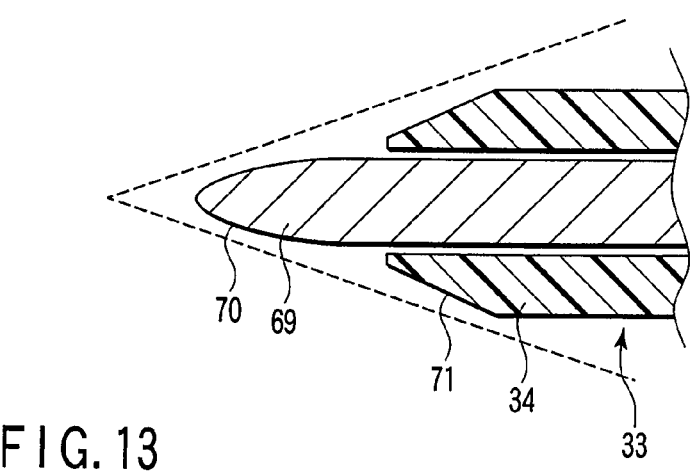
FIG. 13 is a longitudinal sectional view showing the distal ends of the endoscope and the insertion aid instrument in the first referential embodiment of the present invention.

FIGS. 12 and 13 show a first referential embodiment of the present invention.

In the placement method of the embodiments described above, the endoscope 33 has to pass the narrow cervical canal 32 of the uterine cervix 31 when the endoscope 33 is inserted into the uterine cavity 27. In the above-described endoscope 33, the outside diameter of the endoscope insertion portion 34 is generally greater than the inside diameter of the cervical canal 32. The cervical canal 32 can be previously expanded using a plurality of expansion instruments in multiple steps in order to insert the endoscope insertion portion 34 into the uterine cavity 27 via the cervical canal 32, but in a placement system of the present referential embodiment, an insertion aid instrument mechanism different from the expansion instrument is added to the placement system of the first to fifth embodiments.

An insertion aid instrument 69 of the insertion aid instrument mechanism is a rod-like member thinner than the cervical canal 32. A first tapered surface 70 whose outside diameter increases from the distal end to proximal end side is formed at the distal end of the insertion aid instrument 69, and the distal end of the insertion aid instrument 69 includes a cone-like shape with a round top. The outside diameter of the insertion aid instrument 69 is substantially equal to the inside diameter of the accessory channel 46 of the endoscope 33, and the insertion aid instrument 69 is inserted through the accessory channel 46 and movable forward and backward. The accessory channel 46 extends along the central axis of the endoscope insertion portion 34 in the endoscope insertion portion 34 and the channel opening 47 is disposed at the distal end of the endoscope insertion portion 34 at the position of the central axis of the endoscope insertion portion 34. At the distal end of the endoscope insertion portion 34, a second tapered surface 71 whose outside diameter increases from the peripheral portion of the channel opening 47 to the proximal side is formed, and the distal end of the endoscope insertion portion 34 includes a truncated cone-like shape. The first tapered surface 70 of the insertion aid instrument 69 and the second tapered surface 71 of the endoscope 33 are formed so that they are smoothly connected to each other to form one conical surface as a whole when the distal end of the insertion aid instrument 69 is projected from the channel opening 47.

In the placement method of the present embodiment, when the endoscope insertion portion 34 is inserted into the uterine cavity 27 via the cervical canal 32, the insertion aid instrument 69 is inserted through the accessory channel 46 of the endoscope 33 so that the distal end of the insertion aid instrument 69 is projected from the channel opening 47 and held. Then, the insertion aid instrument 69 and the endoscope insertion portion 34 are sequentially inserted into the cervical canal 32, and the endoscope insertion portion 34 is inserted into the uterine cavity 27 beyond the cervical canal 32 while the cervical canal 32 is being expanded by the first and second tapered surfaces 70 and 71.

Figure 14:
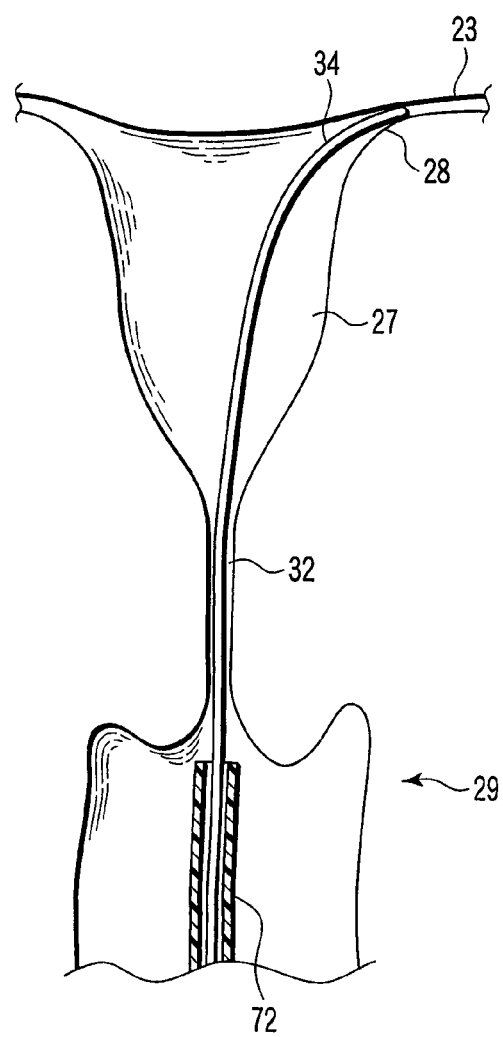
FIG. 14 is a schematic diagram showing an insertion step of a placement method in a second referential embodiment of the present invention.
Figure 15:
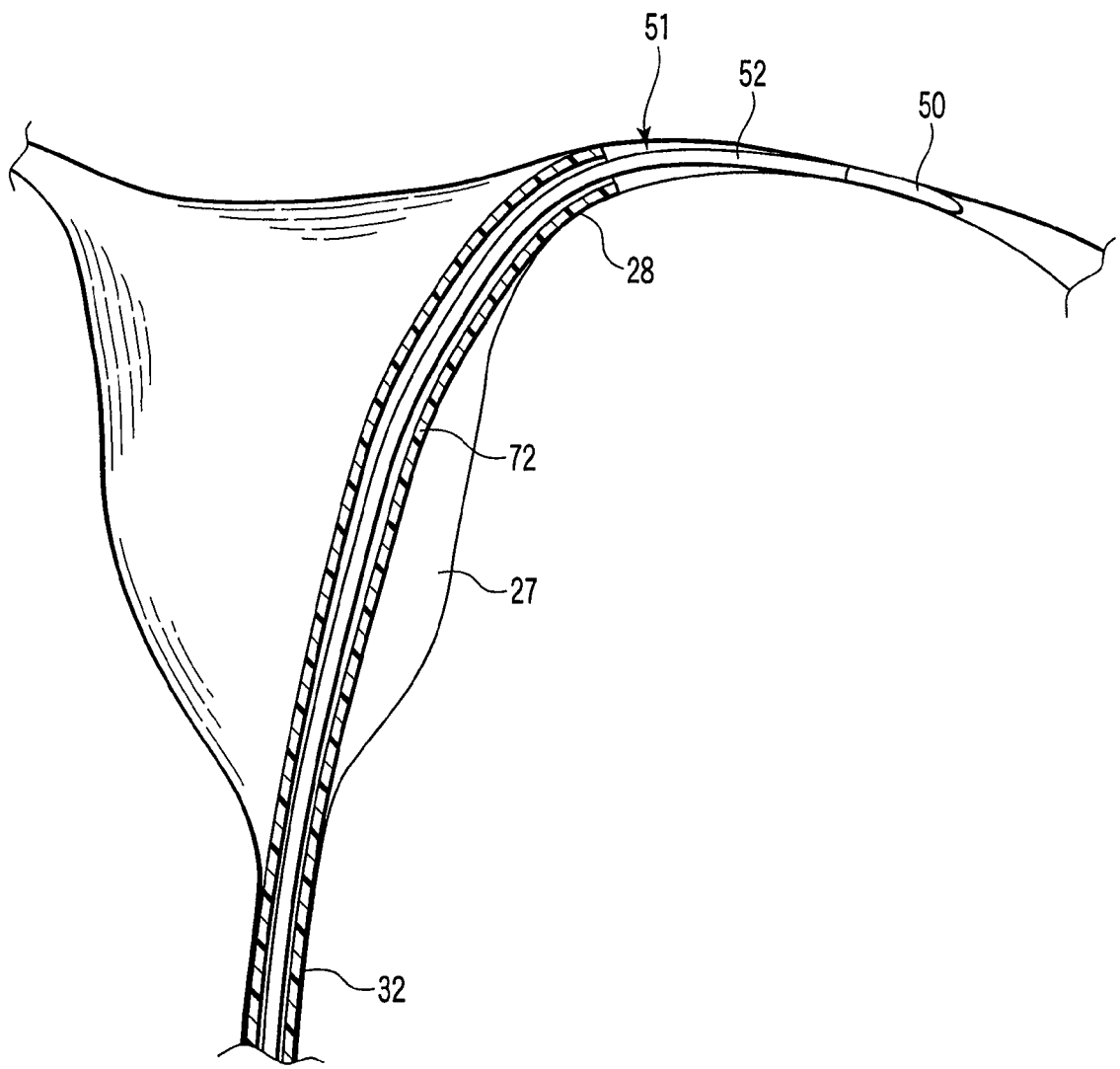
FIG. 15 is a schematic diagram showing a placement step of the placement method in the second referential embodiment of the present invention.

FIGS. 14 and 15 show a second referential embodiment of the present invention.

An endoscope 33 in the present referential embodiment includes no accessory channel 46, and the outside diameter of the endoscope insertion portion 34 is smaller than the inside diameter of the cervical canal 32. That is, the endoscope insertion portion 34 can directly pass through the cervical canal 32. Moreover, the placement system of the present referential embodiment includes an outer sheath 72 through which the endoscope insertion portion 34 or an insertion portion 52 of the placement instrument 51 is inserted to be movable forward and backward. The distal end of the outer sheath 72 is configured to be inserted into the uterine tube ostium 28 and fitted into the uterine tube 23 such that the uterine tube 23 can be sealed from the uterine cavity 27. Further, the placement system includes the pressurization device 55 and the detection device 56 similar to those in the first or second embodiment, and the proximal end of the connecting tube 62 is connectable to the proximal end of the outer sheath 72.

In a placement method of the present embodiment, the endoscope insertion portion 34 is previously inserted through the outer sheath 72. The outer sheath 72 and the endoscope insertion portion 34 are inserted into the vagina 29, and the distal ends of the outer sheath 72 and the endoscope insertion portion 34 are placed face to the entrance of the cervical canal 32. Then, as shown in FIG. 14, the endoscope insertion portion 34 is moved forward with respect to the outer sheath 72 to project the endoscope insertion portion 34 from the distal end of the outer sheath 72, and the endoscope insertion portion 34 is inserted into the uterine cavity 27 via the cervical canal 32. Then, the distal end of the endoscope insertion portion 34 is lightly pushed into the uterine tube ostium 28. Further, the outer sheath 72 is inserted beyond the cervical canal 32 up to the uterine cavity 27 along the endoscope insertion portion 34, and the distal end of the outer sheath 72 is further inserted into the uterine tube ostium 28 along the endoscope insertion portion 34 and fitted into the uterine tube 23. Then, the endoscope insertion portion 34 is removed from the outer sheath 72. Subsequently, as shown in FIG. 15, the insertion portion 52 of the placement instrument 51 is inserted through the outer sheath 72, and the insertion portion 52 is projected from the distal end of the outer sheath 72, so that the distal end of the insertion portion 52 is inserted into the uterine tube 23, and a blocking tube 50 is placed in the uterine tube 23. Then, the insertion portion 52 is removed from the outer sheath 72. Further, the pressurization device 55 and the detection device 56 are connected to the proximal end of the outer sheath 72, and whether the blocking tube 50 is properly placed in the uterine tube 23 is checked as in the first or second embodiment. In addition, the endoscope insertion portion 34 may be again inserted through the outer sheath 72 and the distal end of the endoscope insertion portion 34 may be inserted up to the uterine tube ostium 28 to check by the endoscope 33 whether the blocking tube 50 is properly placed.

In addition, while air is used to pressurize the detection target space in the embodiments described above, various kinds of gases or liquids can be used. For example, a physiological salt solution can be used as a pressurization medium.

Furthermore, the present invention is not limited to the contraceptive operation which blocks the uterine tube, and can be applied to various procedures wherein a placement member is placed in a tubular tissue in a body to block the tubular tissue. For example, the present invention can be applied to a hepatic artery embolization wherein a hepatic artery is blocked to stop blood flow to cancer cells and destroy the cancer cells, and an emphysema treatment wherein a bronchial tube is blocked to cause the return of air.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A placement method comprising:
    inserting an endoscope into a uterine tube through a uterine cavity;
    placing a placement member, which is placed in the uterine tube and blocks the uterine tube, in the uterine tube via a channel of the endoscope;
    blocking the uterine tube at the position closer to the uterine cavity than the placement member with a distal end of the endoscope;
    pressurizing a detection target space between the placement member and the distal end of the endoscope via the channel of the endoscope;
    detecting a pressure state variation over time in the detection target space; and
    judging whether the uterine tube is securely blocked by the placement member and whether the placement member is disposed at an appropriate placement position based on the pressure variations over time in the detection target space.

2. The placement method according to claim 1, comprising:
    the inserting;
    the blocking;
    placing the placement member in the tubular tissue via the channel of the endoscope;
    the pressurizing; and
    the detecting.

3. The placement method according to claim 1, comprising:
    previously placing the placement member in the tubular tissue via the channel of the endoscope;
    the inserting;
    the blocking;
    the pressurizing; and
    the detecting.

4. The placement method according to claim 1, wherein the blocking includes fitting the distal end of the endoscope into the uterine tube.

5. The placement method according to claim 1, wherein the pressurizing includes supplying a fluid into the detecting target space via the channel of the endoscope.

6. The placement method according to claim 1, wherein the detecting includes detecting a pressure value in the detecting target space.

7. The placement method according to claim 1, wherein the detecting includes connecting an inside of an elastic bag member disposed outside the endoscope with the detecting target space via the channel of the endoscope.

8. The placement method according to claim 1, wherein the endoscope includes a flexible scope.

* * * * *